US012806315B2

(12) United States Patent
Klassen

(10) Patent No.: US 12,806,315 B2
(45) Date of Patent: Nov. 24, 2026

(54) BIOMATRIX-IMPREGNATED POROUS CONDUIT FOR TISSUE ENGINEERING

(71) Applicant: IVIVA Medical, Inc., Medford, MA (US)

(72) Inventor: Charles C. Klassen, Jamaica Plain, MA (US)

(73) Assignee: IVIVA Medical, Inc., Medford, MA (US)

( * ) Notice: Subject to any disclaimer, the term of this patent is extended or adjusted under 35 U.S.C. 154(b) by 536 days.

(21) Appl. No.: 18/278,608

(22) PCT Filed: Feb. 23, 2022

(86) PCT No.: PCT/US2022/017588
§ 371 (c)(1),
(2) Date: Aug. 23, 2023

(87) PCT Pub. No.: WO2022/182805
PCT Pub. Date: Sep. 1, 2022

(65) Prior Publication Data

US 2024/0139381 A1 May 2, 2024

Related U.S. Application Data

(60) Provisional application No. 63/152,749, filed on Feb. 23, 2021.

(51) Int. Cl.
*A61F 2/02* (2006.01)
*A61F 2/06* (2013.01)
(Continued)

(52) U.S. Cl.
CPC ............... *A61L 27/56* (2013.01); *A61L 27/16* (2013.01); *A61L 27/222* (2013.01); *A61L 27/24* (2013.01);
(Continued)

(58) Field of Classification Search
CPC ........ A61F 2/02; A61F 127/24; A61F 127/48; A61F 2/06; A61F 2/82; A61F 2002/30766; A61F 2/2418; A61L 27/56; A61L 27/16
See application file for complete search history.

(56) References Cited

U.S. PATENT DOCUMENTS

| | | | | |
|---|---|---|---|---|
| 5,665,114 A | 9/1997 | Weadock et al. | | |
| 6,537,567 B1 * | 3/2003 | Niklason | ............... | C12M 21/08 435/395 |

(Continued)

FOREIGN PATENT DOCUMENTS

| | | | | |
|---|---|---|---|---|
| AU | 2007251370 A1 * | 11/2007 | ............. | A61L 27/38 |
| EP | 0698395 A1 | 2/1996 | | |

(Continued)

OTHER PUBLICATIONS

International Search Report for Application No. PCT/US2022/017588 mailed May 13, 2022.

(Continued)

*Primary Examiner* — Seema Mathew
(74) *Attorney, Agent, or Firm* — Morse, Barnes-Brown & Pendleton, P.C.; Lisa M. Warren, Esq.; Daniel L. Branson, Esq.

(57) ABSTRACT

Disclosed herein is a conduit embedded with a biocompatible polymer for use in devices such as artificial tissues and organs. Also disclosed are methods of making such conduits.

10 Claims, 4 Drawing Sheets

(51) Int. Cl.

| | |
|---|---|
| ***A61L 27/16*** | (2006.01) |
| ***A61L 27/22*** | (2006.01) |
| ***A61L 27/24*** | (2006.01) |
| ***A61L 27/36*** | (2006.01) |
| ***A61L 27/38*** | (2006.01) |
| ***A61L 27/48*** | (2006.01) |
| ***A61L 27/56*** | (2006.01) |

(52) U.S. Cl.

CPC ....... *A61L 27/3633* (2013.01); *A61L 27/3804* (2013.01); *A61L 27/48* (2013.01); *A61L 2400/18* (2013.01)

(56) References Cited

U.S. PATENT DOCUMENTS

| | | | | |
|---|---|---|---|---|
| 8,415,159 | B2 | 4/2013 | Ward et al. | |
| 9,622,849 | B2 | 4/2017 | El-Kurdi et al. | |
| 11,284,987 | B2 * | 3/2022 | Sostek | A61F 2/02 |
| 12,661,433 | B2 * | 6/2026 | Shah | A61L 27/54 |
| 2004/0166169 | A1 * | 8/2004 | Malaviya | A61L 27/3645 424/551 |
| 2005/0137677 | A1 | 6/2005 | Rush | |
| 2005/0272153 | A1 * | 12/2005 | Xuenong | A61L 27/3608 435/395 |
| 2006/0149363 | A1 | 7/2006 | Kujawski | |
| 2008/0063627 | A1 * | 3/2008 | Stucke | A61L 27/54 435/325 |
| 2013/0006349 | A1 * | 1/2013 | Chun | B32B 5/022 435/395 |
| 2013/0013083 | A1 * | 1/2013 | Blum | A61L 27/60 623/23.7 |
| 2013/0218253 | A1 * | 8/2013 | Kaufmann | A61L 31/146 623/1.2 |
| 2013/0345824 | A1 * | 12/2013 | Dahl | A61L 27/3633 435/68.1 |
| 2015/0094808 | A1 * | 4/2015 | Macchiarini | A61L 27/54 435/395 |
| 2015/0359621 | A1 * | 12/2015 | Sostek | A61F 2/02 623/23.72 |
| 2016/0287756 | A1 * | 10/2016 | Lewis | B33Y 10/00 |
| 2018/0243477 | A1 * | 8/2018 | Srouji | A61L 27/56 |
| 2019/0321158 | A1 * | 10/2019 | Quint | A61K 35/44 |
| 2019/0336647 | A1 * | 11/2019 | Klassen | A61L 27/18 |
| 2019/0343985 | A1 * | 11/2019 | Zreiqat | A61L 27/52 |
| 2020/0078160 | A1 * | 3/2020 | Magin | A61L 27/24 |
| 2020/0354533 | A1 * | 11/2020 | Tuszynski | B32B 1/00 |
| 2021/0236693 | A1 * | 8/2021 | Manavitehrani | A61L 27/365 |
| 2022/0023496 | A1 * | 1/2022 | Xie | A61L 27/18 |
| 2022/0354992 | A1 * | 11/2022 | Reiterer | A61F 2/0063 |

FOREIGN PATENT DOCUMENTS

| | | | | | |
|---|---|---|---|---|---|
| JP | 2004523484 | A | * | 8/2004 | A61L 31/041 |
| WO | WO-0249536 | A2 | * | 6/2002 | D01D 5/0069 |
| WO | WO-2006044904 | A2 | * | 4/2006 | A61L 27/3878 |
| WO | 2006/074300 | A1 | | 7/2006 | |
| WO | WO-2007048831 | A2 | * | 5/2007 | A61L 27/56 |
| WO | WO-2007104965 | A2 | * | 9/2007 | A61L 27/58 |
| WO | WO-2018112480 | A1 | * | 6/2018 | A61L 27/54 |
| WO | 2019/157583 | A1 | | 8/2019 | |
| WO | WO-2020035703 | A1 | * | 2/2020 | A61L 27/3834 |

OTHER PUBLICATIONS

Gruionu, et al., "Encapsulation of ePTFE in prevascularized collagen leads to peri-implant vascularization with reduced inflammation," Journal of Biomedical Materials Research A, 95A(3), Dec. 2010.

* cited by examiner

BIOMATRIX-IMPREGNATED POROUS CONDUIT FOR TISSUE ENGINEERING

CROSS-REFERENCE TO RELATED APPLICATIONS

This application is a national stage filing under 35 U.S.C. 371 of International Application No. PCT/US2022/017588, filed Feb. 23, 2022, which claims the benefit of U.S. Provisional Application No. 63/152,749, filed on Feb. 23, 2021, the contents of which are hereby incorporated by reference in their entirety. International Application No. PCT/US2022/017588 was published under PCT Article 21(2) in English.

BACKGROUND OF THE INVENTION

Vascular perfusion supplies organs with blood and allows for functions such as gas and solute exchange. Similar luminal structures (i.e., "tubes") permit similar functions such as waste removal, etc. In native tissue, these tubes depend on the highly organized structure of their collagen fibers to provide mechanical strength and durability. These highly refined mechanics allow for thin vessel walls that can withstand pressures of hundreds and sometimes thousands of mmHg and are able to be sutured without ripping, yet remain compliant and soft, as well as permissive for cell growth.

In order to develop engineered tissues and specifically vasculature that can replicate and replace native function, similarly robust conduit structures for engineered scaffolds are needed. This has proven extremely challenging, with limited progress to date; however, sophisticated approaches toward standalone engineered vascular grafts and vessels are starting to show promise (see Dahl, et al (2011) Science Translational Medicine, 3(68), 68ra9-68ra9). These grafts are fabricated with collagen layers similar to native vessels which gives them substantial strength, however the way they are made prohibits integration and/or co-fabrication with engineered organ tissue or cells. Despite their sophisticated nature, these grafts are not integrated with scaffold structures that could provide function, and indeed they are purposefully developed only as standalone vessels for anastomosis with native vasculature. In order to create organ scaffolds with fully integrated vasculature capable of meeting the demands of native physiology, it is necessary to develop a vessel of similar composition that can be fabricated in parallel or ideally in situ within an engineered organ scaffold.

This presents a number of significant challenges since the materials most suited for cellular engineering (hydrogels and native extracellular matrix derivatives) are ill-suited for constructing a mechanically robust conduit. Attempts at reinforcement have centered around synthetic meshes and other materials which provide a support structure, but the macroscale nature of the material architecture and the interface with the hydrogel prevent development of a unified tubular structure, and these grafts suffer from mechanical instability. These limited attempts at developing a tubular structure to interface with engineered scaffolds have left most sophisticated engineered tissue scaffolds to rely on a surrounding chamber or other artificial extraneous construct for sustained perfusion (see, Homan, et al. (2016) Sci Rep 6, 34845). Attempts at fastening artificial or bioartificial tubes to engineered scaffolds fail due to poor bond and mechanical mismatch between tube and bulk material. In order to push the development of engineered fully biologic vasculature and organ scaffolds forward, it is critical to develop an approach for vessel construction that is flexible and easily integrated into a variety of fabrication approaches. Beyond replicating vessels and luminal structures in engineered tissue, there are many potential in vitro uses for mechanically stable hydrogel-based engineered tubular structures, such as replicating biologic function, physiology, or developmental processes.

SUMMARY OF THE INVENTION

Herein we present a novel solution whereby a mechanically robust tubular structure is fabricated using a highly microporous (up to and exceeding 80% porosity, pore size of 0.1-0.5 μm) support structure of expanded synthetic polymer such as polytetrafluorethylene tubing (ePTFE). Low porosity, thick-walled configurations of ePTFE, are used as acellular vascular grafts and have been implanted for decades, providing a deep pool of data on biocompatibility, making ePTFE an ideal material for tissue engineering. In addition to standalone configurations of the tubular structure, this novel process allows for integration of the support structure and co-fabrication of the tubular vessel in a holistic manner within the fabrication process of an engineered tissue scaffold or construct. This produces a unified end-product that has mechanically stable vasculature and tubular structures capable of meeting the performance requirements for implantation, yet is also a mechanically and materially cohesive structure. This novel solution overcomes current challenges with engineered vessels and perfusion of engineered tissue.

BRIEF DESCRIPTION OF THE DRAWINGS

FIG. 2A provides SEM and optical microscopy images of ePTFE tubing. FIG. 2B shows the porosity of ePTFE tubing as a function of density and pore size.

DETAILED DESCRIPTION OF THE INVENTION

Figure 1:
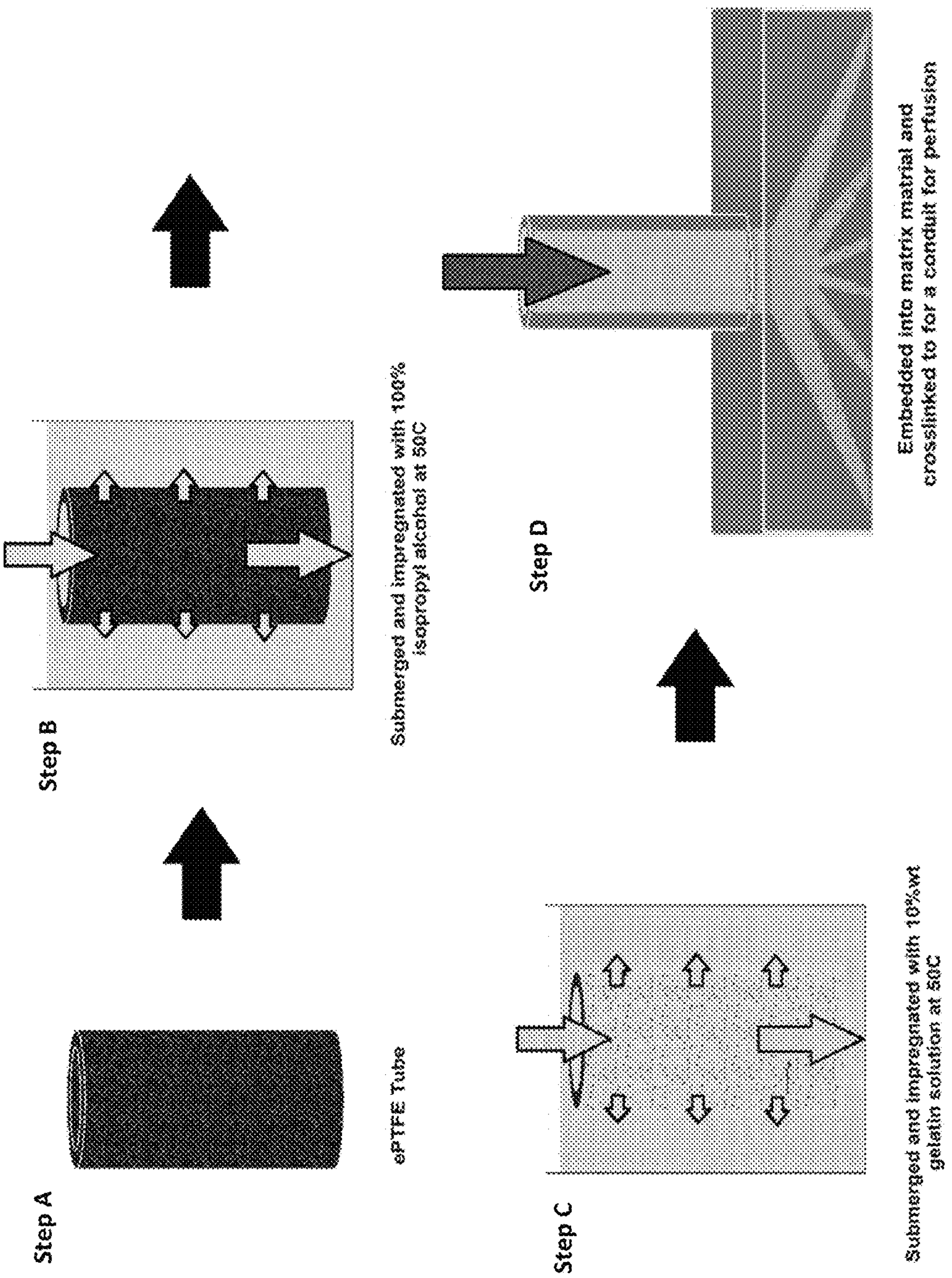
FIG. 1 shows a schematic for manufacturing a conduit as an embodiment of the present invention. The method of manufacturing comprises Step A: providing a tubular structure having an internal luminal space and comprising a porous biocompatible polymer, Step B: perfusing the pores and luminal space of the tubular structure with a first solution, Step C: replacing the first solution by perfusing the pores and luminal space of the tubular structure with the aqueous solution comprising liquified extracellular matrix material, and Step D: embedding the tubular structure in extracellular matrix material by polymerizing the liquified extracellular matrix material to form the conduit.
Figure 2B:
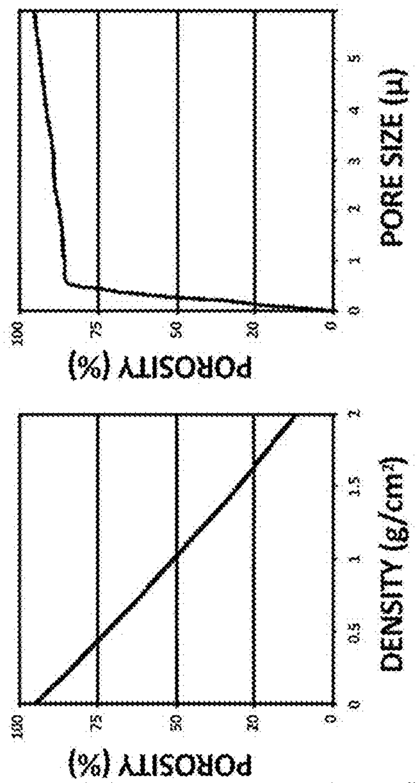
FIGS. 2A-2B show porosity polytetrafluorethylene tubing (ePTFE).
Figure 2A:
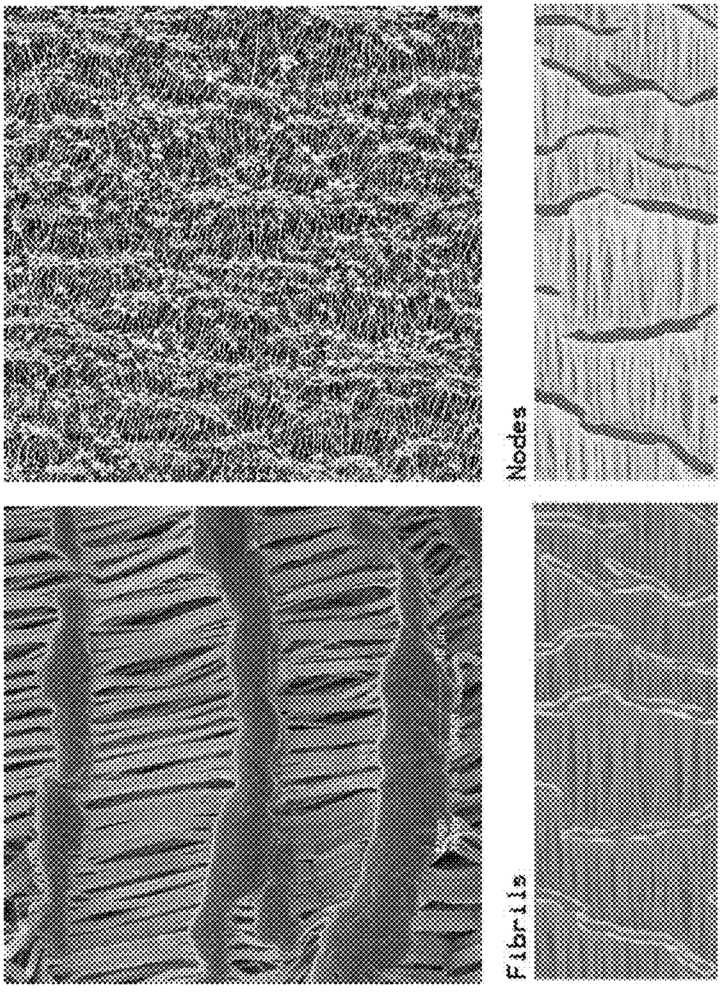
Figure 3:
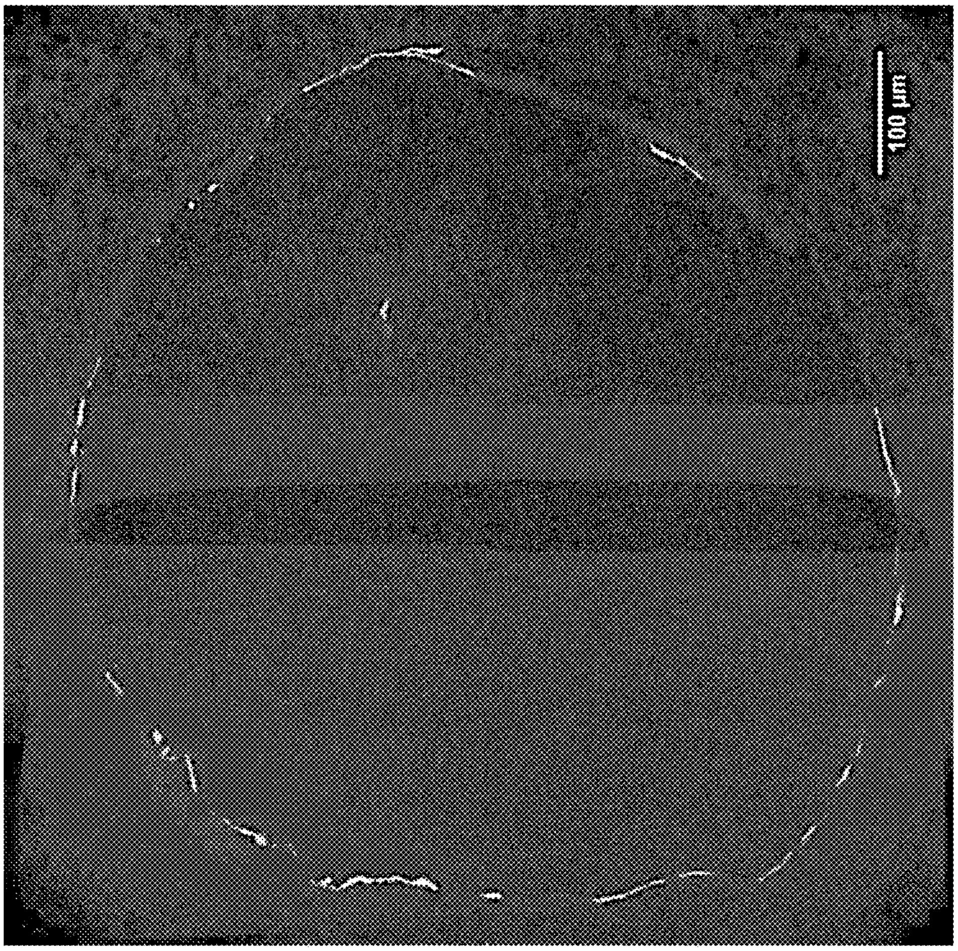
FIG. 3 shows the histology (cross-section) of fabricated tubular constructs seeded and cultured with GFP+ HUVEC cells providing full endothelial coverage.
Figure 4:
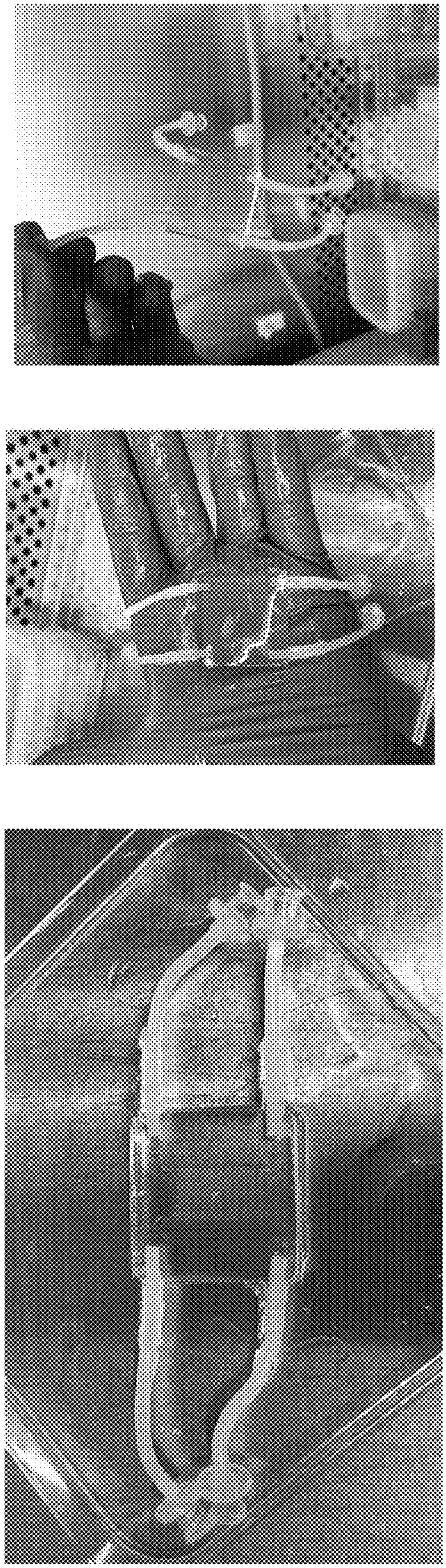
FIG. 4 shows images of an engineered construct embodiment of the invention fabricated with ePTFE tubular conduits.

Some aspects of the present disclosure are directed to a conduit having a tubular structure comprising a porous biocompatible polymer embedded in a biocompatible extracellular matrix material, and an internal luminal space.

The porous biocompatible polymer is not limited and may be any suitable porous biocompatible polymer. In some embodiments, the porous biocompatible polymer comprises or consists of polytetrafluorethylene, polydimethylsiloxane, polycarbonate, or silicone. In some embodiments, the porous biocompatible polymer is expanded polytetrafluorethylene.

The pore size of the pores in the biocompatible polymer is not limited and may be any suitable pore size. In some embodiments, the average or median pore size (i.e., pore diameter) is about 0.1 μm, 0.15 μm, 0.2 μm, 0.25 μm, 0.3 μm, 0.35 μm, 0.4 μm, 0.45 μm, or about 0.5 μm. In some embodiments, the average or median pore size is about 0.1 to 0.5 μm. The porosity (i.e., the fraction of the volume of voids over the total volume) of the porous biocompatible polymer is also not limited and may be any suitable porosity. In some embodiments, the porosity is at least 10%, 20%, 30%, 40%, 50%, 60%, 70%, 80%, 90%, 95%, 99%, or more. In some embodiments, the porosity is greater than 50%. In some embodiments, the porosity is between 50%-60%, 50%-70%, or 50% to 80%.

The biocompatible extracellular matrix material is not limited and may be any suitable biocompatible extracellular matrix material known in the art. The biocompatible extracellular matrix material may be biologic, synthetic, or composite materials such as collagen, decellularized native extracellular matrix, gelatin, gelatin methacryloyl, other hydrogels, cellulose, or other materials. In some embodiments, the biocompatible extracellular matrix material is polymerized. In some embodiments, the biocompatible extracellular matrix material comprises a polymerized material selected from gelatin, gelatin methacryloyl, collagen, or decellularized native extracellular matrix.

The internal luminal space of the conduit may be any suitable shape for connection to a biological fluid supply (e.g., a blood vessel, a lymph duct, a renal collecting duct, a bronchiole, an endocrine or hormone duct, etc.). In some embodiments, the internal luminal space has a long axis. In some embodiments, the internal luminal space is cylindrical or roughly cylindrical. In some embodiments, the internal luminal space has a diameter (e.g., on the long axis) of 0.1 to 10 cm. In some embodiments, the internal luminal space has a diameter (e.g., on the long axis) of 0.1 to 1 cm. In some embodiments, the internal luminal space has a diameter (e.g., on the long axis) of 0.1 to 0.5 cm. In some embodiments, the internal luminal space has a diameter (e.g., on the long axis) of at least 0.1 cm, 0.2 cm, 0.3 cm, 0.5 cm, or 1 cm.

In some embodiments, the conduit further comprises mammalian cells. The mammalian cells are not limited and may be any suitable mammalian cells. In some embodiments, the mammalian cells are epithelial or endothelial cells. In some embodiments, the mammalian cells are selected from smooth muscle cells, fibroblasts, and/or endothelial cells. In some embodiments, the mammalian cells comprise at least 2, at least 3, at least 4, or more cell types. In some embodiments, the mammalian cells comprise or consist of one or more of human vascular endothelial cells, human renal epithelial cells, human intestinal epithelial cells, human endocrine cells, or human epithelial cells.

In some embodiments, the conduit is not attached to another structure (e.g., the conduit prior to use). In some embodiments, one end of the conduit is attached (e.g., surgically anastomosed to) to an artificial tissue scaffold. In some embodiments, the conduit is attached at one end to native tissue (e.g., a blood vessel, a lymph duct, a renal collecting duct, a bronchiole, an endocrine or hormone duct, etc.). In some embodiments, the conduit is attached at both ends to native tissue (e.g., a blood vessel, a lymph duct, a renal collecting duct, a bronchiole, an endocrine or hormone duct, etc.). In some embodiments, one or both ends of the conduit are surgically anastomosed to native vasculature in vivo.

Some aspects of the present disclosure are related to a device comprising the conduit described herein. In some embodiments, the device comprises the conduit as described herein having a first end embedded (e.g., embedded and integrated) in a tissue scaffold. In some embodiments, the tissue scaffold comprises the same biocompatible extracellular matrix material as the conduit and a vascular channel system. In some embodiments, the luminal space of the conduit is configured to be in fluid communication with the vascular channel system. The tissue scaffold is not limited. In some embodiments, the tissue scaffold is a tissue scaffold described in PCT publication No.: WO 2018/112480, published Jun. 21, 2018, incorporated herein by reference in its entirety. In some embodiments, the tissue scaffold comprises one or more mammalian cell types. The mammalian cell types are not limited and may be a mammalian cell type described herein.

Some aspects of the present disclosure are related to a device comprising a tissue scaffold and a conduit, wherein the tissue scaffold comprises a biocompatible extracellular matrix material and a vascular channel system, the conduit comprises a tubular structure comprising a porous biocompatible polymer embedded in the biocompatible extracellular matrix material, and an internal luminal space, wherein the tubular structure has a first end embedded and integrated into the biocompatible extracellular matrix material of the tissue scaffold and a second end configured to connect to a fluid supply, and wherein the luminal space is configured to be in fluid communication with the fluid supply and the vascular channel system. The conduit is not limited and may be any suitable conduit described herein. The tissue scaffold is also not limited and may be any suitable tissue scaffold described herein. The biocompatible extracellular matrix material is also not limited and may be any suitable biocompatible extracellular matrix material described herein. In some embodiments, the tissue scaffold comprises one or more mammalian cell types. The mammalian cell types are not limited and may be a mammalian cell type described herein.

The porous biocompatible polymer is not limited and may be any porous biocompatible polymer described herein. In some embodiments, the porous biocompatible polymer is expanded polytetrafluorethylene.

The pore size of the porous biocompatible polymer is not limited and may be any pore size described herein. In some embodiments, the porous biocompatible polymer comprises pores having a pore size of 0.1 to 10 μm in diameter and a porosity of greater than 50%.

In some embodiments, the biocompatible extracellular matrix material is polymerized and comprises gelatin, gelatin methacryloyl, collagen, or decellularized native extracellular matrix.

The internal luminal space of the conduit may be any suitable shape for connection to a biological fluid supply (e.g., a blood vessel, a lymph duct, a renal collecting duct, a bronchiole, an endocrine or hormone duct, etc.). In some embodiments, the internal luminal space has a long axis. In some embodiments, the internal luminal space is cylindrical or roughly cylindrical. In some embodiments, the internal luminal space has a diameter (e.g., on the long axis) of 0.1 to 10 cm. In some embodiments, the internal luminal space has a diameter (e.g., on the long axis) of 0.1 to 1 cm. In some embodiments, the internal luminal space has a diameter (e.g., on the long axis) of 0.1 to 0.5 cm. In some embodiments, the internal luminal space has a diameter (e.g., on the long axis) of 0.3 to 0.7 cm. In some embodiments, the internal luminal space has a diameter (e.g., on the long axis) of at least 0.1 cm, 0.2 cm, 0.3 cm, 0.5 cm, 0.6 cm, 0.8 cm, 0.9 cm, or 1 cm.

In some embodiments, the conduit further comprises mammalian cells, optionally selected from smooth muscle cells, fibroblasts, and/or endothelial cells.

The volume of the vascular channel system is not limited and may be any suitable volume for use when implanted in vivo or for use extracorporeally or in in vitro applications. In some embodiments, the vascular channel system has a volume of about 0.01 mL to about 10 L. In some embodiments, the vascular channel system has a volume of about 0.01 mL to about 100 ml, about 0.1 mL to about 10 ml, or 1 mL to 100 mL, or any range in between. In some embodiments, the vascular channel system is described in WO 2018/112480, published Jun. 21, 2018, or WO 2018/227026, published Dec. 13, 2018

The disclosed device may have a single conduit (e.g., wherein the biological fluid diffuses in and out of the cell scaffold through the conduit, e.g., replicating an endocrine gland function) or more than one conduit. In some embodiments, the device comprises a second conduit having a second luminal space, a first end embedded (e.g., embedded and integrated) in the biocompatible extracellular matrix material of the tissue scaffold, and a second end configured to connect to a fluid outlet, wherein the luminal space, vascular channel system and second luminal space are configured to be in fluid communication with each other, the fluid supply, and the fluid outlet. Such device could, e.g., be used to shunt a biological fluid such as blood through the vascular channel system to add a desired substance such as a hormone, cytokine, or endocrine substance produced by cells in the vascular channel system.

In some embodiments, the device comprises a membrane that separates the vascular channel system from a second vascular channel system. The membrane is not limited and may be any suitable membrane. In some embodiments, the membrane is described in WO 2018/112480, published Jun. 21, 2018, or WO 2018/227026, published Dec. 13, 2018, herein incorporated by reference in their entireties. In some embodiments, the second vascular channel system is fluidly connected to a conduit as described herein. In some embodiments, the second vascular system is fluidly connected to two conduits as described herein. In some specific embodiments, the device further comprises a membrane, a second vascular channel system, a third conduit having a third luminal space, and a fourth conduit having a fourth luminal space, wherein the vascular channel system and the second vascular channel system are configured to be in fluid communication across the membrane, the third conduit has a first end embedded (e.g., embedded and integrated) in the biocompatible extracellular matrix of the tissue scaffold and a second end configured to connect to a second fluid supply, the fourth conduit has a first end embedded (e.g., embedded and integrated) in the biocompatible extracellular matrix of the tissue scaffold and a second end configured to connect to a second fluid outlet, and the third luminal space, second vascular channel system, and fourth luminal space are configured to be in fluid communication with each other, the second fluid supply, and the second fluid outlet. In some embodiments, the device further comprises mammalian cells as described herein in one or more of the first through fourth conduits, the first vascular channel system, and the second vascular channel system. In some embodiments, the device is surgically anastomosed into a vascular or other channel system of a subject, e.g., to replace or enhance renal function, pulmonary function, endocrine gland function, digestive tract function, lymph function, etc.

Some aspects of the present disclosure are directed to a method of manufacturing a conduit or device as described herein. In some embodiments, the method of manufacturing the conduit comprises providing a tubular structure having an internal luminal space and comprising a porous biocompatible polymer, perfusing the pores and luminal space of the tubular structure with a first solution, replacing the first solution by perfusing the pores and luminal space of the tubular structure with the aqueous solution comprising liquified extracellular matrix material, and embedding the tubular structure in extracellular matrix material by polymerizing the liquified extracellular matrix material to form the conduit. In some embodiments, the method further comprises providing a tissue scaffold (e.g., a tissue scaffold as described herein) comprising the extracellular matrix material and embedding (e.g., embedding and integrating) a first end of the conduit in the extracellular matrix material of the tissue scaffold. In some embodiments, the tissue scaffold further comprises a vascular channel system and the first end is embedded in the extracellular matrix material so that the luminal space is configured to be in fluid communication with the vascular channel system.

In some alternate embodiments, the steps of perfusing the pores and luminal space of the tubular structure with a first solution and replacing the first solution by perfusing the pores and luminal space of the tubular structure with the aqueous solution comprising liquified extracellular matrix material are replaced with a single step wherein the first solution perfuses the pores and luminal space of the tubular structure and contains liquified extracellular matrix material (e.g., the first solution is an aqueous solution comprising liquified extracellular matrix material and a surfactant at a sufficient concentration to enable perfusion into the pores of the tubular structure).

The first solution is not limited and may be any suitable solution compatible with the tubular structure (e.g., not damaging to the tubular structure) and capable of perfusing into the pores and luminal space (e.g., a solution with sufficiently low surface tension, viscosity, etc.) In some embodiments, the first solution is an aqueous solution and comprises a surfactant at a sufficient concentration to enable perfusion into the pores. The surfactant is not limited and may be any suitable surfactant. In some embodiments, the surfactant is sodium lauryl sulfate, sodium dioctyl sulfosuccinate, a polysorbate-type nonionic surfactant (e.g., TWEEN-20, TWEEN-80), Triton X-100, or a combination thereof. In some embodiments, the surfactant is a medically acceptable surfactant. In some embodiments, the first solution is nonpolar and miscible in the aqueous solution comprising the liquified extracellular matrix material.

The porous biocompatible polymer is not limited and may be any suitable porous biocompatible polymer described herein. In some embodiments, the porous biocompatible polymer is expanded polytetrafluorethylene. In some embodiments, the porous biocompatible polymer comprises pores having a pore size of 01. to 10 μm in diameter and a porosity of greater than 50%. In some embodiments, the biocompatible extracellular matrix material is polymerized and comprises gelatin, gelatin methacryloyl, collagen, or decellularized native extracellular matrix.

In some embodiments, the internal luminal space of the conduit has a diameter of 0.1 to 10 cm.

In some embodiments, the method further comprises adding (e.g. seeding) mammalian cells to the vascular channel system and/or the conduit. The mammalian cells are not limited and may be any mammalian cell or mixture of mammalian cells described herein. In some embodiments, the mammalian cells are selected from smooth muscle cells, fibroblasts, and/or endothelial cells.

Some embodiments of the methods disclosed herein comprise the following steps:

In step 1, a mechanically robust tubular porous ePTFE structure is sourced, fabricated or manufactured using standard techniques. This structure may be purely tubular in nature, or it may have additional features such as ribbing, flanges, anchor points, or other such architectural additions designed to enhance function or integration with other structures. The amount of void space in this structure, equivalent to the porosity of the tubing, is tunable and may be uniform or may be tailored locally to vary the amount and location of porosity and stiffness in the final composition.

In step 2, the porous structure may be treated with other materials or processes to modify chemical, biological, or physical properties, such as improving hydrophilicity or material surface energy, bioactivity, or other desirable characteristics, in order to aid in fabrication or to enhance the final product.

In step 3, the entirety of the void space in the porous tube structure is impregnated with an initial nonpolar solution that is miscible with aqueous solutions. This may be done by immersion, or by flowing solution through the porous structure aided by vacuum, pressure, sonication, or other techniques.

In step 4, the initial nonpolar solution is replaced with a primary aqueous solution. This may be done by similar techniques as described in step 3.

In step 5, a secondary material solution is used to replace the aqueous solution. This secondary material may or may not contain cells or other biologic material as determined by the final application. This secondary material may be biologic, polymer, composite, or other composition, but must be in a liquid form. This may be done through similar processes as described in steps 3 and 4 and occur in isolation or may occur in conjunction with fabrication of other structures or engineered scaffolds, so as to integrate the tubular structure into a perfusable construct.

In step 6, the material is polymerized, gelled, crosslinked, bonded, or otherwise made solid within the interconnected porous structure of the ePFTE tubing. If necessary, the lumen of the tubing may be cleared prior to or after solidification of the secondary material.

In step 7, the now patent tubular structure may be used as is or may be further processed or incorporated into subsequent structures or engineered tissues. This may be done by molding, casting, or other such techniques. During this process, the secondary material may be impregnated into the porous structure is in contact with similar material in the engineered construct, and is subsequently crosslinked, bonded, cured, or otherwise solidified such that it forms a cohesive uniform single piece of material spanning both the porous structure and some or all of the engineered scaffold. Portions or components of this scaffold may be fabricated prior to integration of the tubular structure, or the tubular structure may serve as a foundation or component for the fabrication of the scaffold.

In step 8, the engineered scaffold is complete, and the lumen of the tubular structure can be accessed via barbed connection, cannulation, surgical anastomosis, or other such means. The porous tubular structure provides a mechanically stable structure for robust connection, enabling flow of liquid or gas into or out of the lumen and anastomosed or attached tissues or vessels.

All patents and other publications identified are expressly incorporated herein by reference for the purpose of describing and disclosing, for example, the methodologies described in such publications that might be used in connection with the present invention. These publications are provided solely for their disclosure prior to the filing date of the present application. Nothing in this regard should be construed as an admission that the inventors are not entitled to antedate such disclosure by virtue of prior invention or prior publication, or for any other reason. All statements as to the date or representation as to the contents of these documents is based on the information available to the applicants and does not constitute any admission as to the correctness of the dates or contents of these documents.

One skilled in the art readily appreciates that the present invention is well adapted to carry out the objects and obtain the ends and advantages mentioned, as well as those inherent therein. The details of the description and the examples herein are representative of certain embodiments, are exemplary, and are not intended as limitations on the scope of the invention. Modifications therein and other uses will occur to those skilled in the art. These modifications are encompassed within the spirit of the invention. It will be readily apparent to a person skilled in the art that varying substitutions and modifications may be made to the invention disclosed herein without departing from the scope and spirit of the invention.

The articles "a" and "an" as used herein in the specification and in the claims, unless clearly indicated to the contrary, should be understood to include the plural referents. Claims or descriptions that include "or" between one or more members of a group are considered satisfied if one, more than one, or all of the group members are present in, employed in, or otherwise relevant to a given product or process unless indicated to the contrary or otherwise evident from the context. The invention includes embodiments in which exactly one member of the group is present in, employed in, or otherwise relevant to a given product or process. The invention also includes embodiments in which more than one, or all of the group members are present in, employed in, or otherwise relevant to a given product or process. Furthermore, it is to be understood that the invention provides all variations, combinations, and permutations in which one or more limitations, elements, clauses, descriptive terms, etc., from one or more of the listed claims is introduced into another claim dependent on the same base claim (or, as relevant, any other claim) unless otherwise indicated or unless it would be evident to one of ordinary skill in the art that a contradiction or inconsistency would arise. It is contemplated that all embodiments described herein are applicable to all different aspects of the invention where appropriate. It is also contemplated that any of the embodiments or aspects can be freely combined with one or more other such embodiments or aspects whenever appropriate. Where elements are presented as lists, e.g., in Markush group or similar format, it is to be understood that each subgroup of the elements is also disclosed, and any element(s) can be removed from the group. It should be understood that, in general, where the invention, or aspects of the invention, is/are referred to as comprising particular elements, features, etc., certain embodiments of the invention or aspects of the invention consist, or consist essentially of, such elements, features, etc. For purposes of simplicity those embodiments have not in every case been specifically set forth in so many words herein. It should also be understood that any embodiment or aspect of the invention can be explicitly excluded from the claims, regardless of whether the specific exclusion is recited in the specification. For example, any one or more active agents, additives, ingredients, optional agents, types of organism, disorders, subjects, or combinations thereof, can be excluded.

Where the claims or description relate to a composition of matter, it is to be understood that methods of making or using the composition of matter according to any of the methods disclosed herein, and methods of using the composition of matter for any of the purposes disclosed herein are aspects of the invention, unless otherwise indicated or unless it would be evident to one of ordinary skill in the art that a contradiction or inconsistency would arise. Where the claims or description relate to a method, e.g., it is to be understood that methods of making compositions useful for performing the method, and products produced according to the method, are aspects of the invention, unless otherwise indicated or unless it would be evident to one of ordinary skill in the art that a contradiction or inconsistency would arise.

Where ranges are given herein, the invention includes embodiments in which the endpoints are included, embodiments in which both endpoints are excluded, and embodiments in which one endpoint is included and the other is excluded. It should be assumed that both endpoints are included unless indicated otherwise. Furthermore, it is to be understood that unless otherwise indicated or otherwise evident from the context and understanding of one of ordinary skill in the art, values that are expressed as ranges can assume any specific value or subrange within the stated ranges in different embodiments of the invention, to the tenth of the unit of the lower limit of the range, unless the context clearly dictates otherwise. It is also understood that where a series of numerical values is stated herein, the invention includes embodiments that relate analogously to any intervening value or range defined by any two values in the series, and that the lowest value may be taken as a minimum and the greatest value may be taken as a maximum. Numerical values, as used herein, include values expressed as percentages. For any embodiment of the invention in which a numerical value is prefaced by "about" or "approximately", the invention includes an embodiment in which the exact value is recited. For any embodiment of the invention in which a numerical value is not prefaced by "about" or "approximately", the invention includes an embodiment in which the value is prefaced by "about" or "approximately".

As used herein "A and/or B", where A and B are different claim terms, generally means at least one of A, B, or both A and B. For example, one sequence which is complementary to and/or hybridizes to another sequence includes (i) one sequence which is complementary to the other sequence even though the one sequence may not necessarily hybridize to the other sequence under all conditions, (ii) one sequence which hybridizes to the other sequence even if the one sequence is not perfectly complementary to the other sequence, and (iii) sequences which are both complementary to and hybridize to the other sequence.

"Approximately" or "about" generally includes numbers that fall within a range of 1% or in some embodiments within a range of 5% of a number or in some embodiments within a range of 10% of a number in either direction (greater than or less than the number) unless otherwise stated or otherwise evident from the context (except where such number would impermissibly exceed 100% of a possible value). It should be understood that, unless clearly indicated to the contrary, in any methods claimed herein that include more than one act, the order of the acts of the method is not necessarily limited to the order in which the acts of the method are recited, but the invention includes embodiments in which the order is so limited. It should also be understood that unless otherwise indicated or evident from the context, any product or composition described herein may be considered "isolated".

As used herein the term "comprising" or "comprises" is used in reference to compositions, methods, and respective component(s) thereof, that are essential to the invention, yet open to the inclusion of unspecified elements, whether essential or not.

As used herein the term "consisting essentially of" refers to those elements required for a given embodiment. The term permits the presence of additional elements that do not materially affect the basic and novel or functional characteristic(s) of that embodiment of the invention.

The term "consisting of" refers to compositions, methods, and respective components thereof as described herein, which are exclusive of any element not recited in that description of the embodiment.

EXAMPLES

Example 1

In one example, the porous tubular structure is a length of expanded polytetrafluorethylene (ePTFE) which is a commercially available and highly tunable biologically inert material initially developed by Gore. By varying the rate and acceleration of expansion during processing (among other parameters) it is possible to achieve tubing with porosity of up to and exceeding 80% which provides a substantial amount of void space for integration of the secondary material. The ePTFE tube has an internal diameter of 3 mm and an outer diameter of 6 mm and is 50 mm long. One end of the ePTFE tubing is placed on a barbed fitting, and the other end is capped with a barbed fitting and closure. The open end of the tubing is connected to a syringe and the tubing is manually filled with a 70% isopropanol solution warmed to 37° C. By pressurizing the lumen of the tubing, the solution is forced out through the wall of the tubing, impregnating the void space and fully evacuating any air from the tubing pores. The tubing is then attached to a syringe or pumping system and is pressurized with a solution containing 10% wt gelatin at 37° C. The pressurization of the tubing forces the solution through the walls of the tubing into the void space occupied by the isopropanol solution, mixing and eventually replacing the solution in the void space entirely with the gelatin solution. Enough volume is passed through the tubing to ensure full evacuation of the isopropanol.

The cap of the tubing is then removed, the tubing is removed from the pump, and the gelatin solution is allowed to drain from the tubing. The syringe is then reattached, the other end of the tubing remains open, and a bolus of 37° C. saline solution is passed through the tubing to remove any separate layer of gelatin remaining inside the tubing and might delaminate later. The tubing is then removed from the barbed fittings and placed in a 4° C. bath of saline solution to cause thermal crosslinking and gelation of the gelatin solution remaining in the void space of the porous tubing. At this point the tubing can be stored, or trimmed and further manipulated for inclusion in downstream fabrication.

The tubing that is impregnated with gelatin is incorporated into a tissue scaffold. Specifically the lumen of the tubing is mated with the sacrificial material that will form the channel structure in the scaffold, and the entire device is molded in a single or series of steps that produce a scaffold with the tubular structure embedded into a similar gelatin material. During the molding process, the gelatin in the scaffold becomes unified and cohesive with the gelatin in the tubular structure, and may be subsequently crosslinked using enzymatic, chemical, or other means. The end result is a gelatin-based scaffold with a single unified hydrogel material that interpenetrates the highly porous tubular support structure, resulting in a mechanically robust tubular structure fabricated in situ during scaffold construction.

In additional examples of this invention, the gelatin solution contains cells, such as smooth muscle cells, fibroblasts, and endothelial cells.

In additional examples of this invention, the tubing is impregnated with GelMA, collagen, decellularized native ECM, or other such biomaterials in addition to or in place of the gelatin solution.

In additional examples of this invention, the tubing is impregnated with different solutions in different areas to achieve variable function or transition from one tissue type or configuration to another.

In additional examples of this invention, the ePTFE tube has a flange and/or barbed features on one end to improve interface surface area and overall integration with a larger construct.

In additional examples of this invention, the ePTFE tubing has variable properties along its length, such as variable porosity or stiffness to improve function.

In additional examples of this invention, the ePTFE tubing has branching structures or tapering along its length to tune perfusion and distribution of fluid.

What is claimed is:

1. A device comprising a tissue scaffold and a conduit, wherein a. the tissue scaffold comprises a biocompatible extracellular matrix material and a vascular channel system, b. the conduit comprises a tubular structure comprising a porous biocompatible polymer embedded in the biocompatible extracellular matrix material of the tissue scaffold, and an internal luminal space, wherein the porous biocompatible polymer has a porosity of greater than 50%, wherein the tubular structure has a first end embedded and integrated into the biocompatible extracellular matrix material of the tissue scaffold and a second end configured to connect to a fluid supply and wherein the luminal space is configured to be in fluid communication with the fluid supply and the vascular channel system.

2. The device of claim 1, wherein the porous biocompatible polymer is expanded polytetrafluorethylene.

3. The device of claim 1, wherein the porous biocompatible polymer comprises pores having a pore size of 0.1 to 10 μm in diameter.

4. The device of claim 1, wherein the biocompatible extracellular matrix material is polymerized and comprises gelatin, gelatin methacryloyl, collagen, or decellularized native extracellular matrix.

5. The device of claim 1, wherein the internal luminal space has a diameter of 0.1 to 10 cm.

6. The device of claim 1, wherein the conduit and/or the vascular channel system further comprises mammalian cells.

7. The device of claim 6, wherein the mammalian cells are selected from the group consisting of smooth muscle cells, fibroblasts, and endothelial cells.

8. The device of claim 1, wherein the vascular channel system has a volume of about 0.01 mL to about 10 L.

9. The device of claim 1, further comprising a second conduit having a second luminal space, a first end embedded in the biocompatible extracellular matrix material of the tissue scaffold, and a second end configured to connect to a fluid outlet, wherein the luminal space, vascular channel system and second luminal space are configured to be in fluid communication with each other, the fluid supply, and the fluid outlet.

10. The device of claim 1, further comprising a membrane, a second vascular channel system, a third conduit having a third luminal space, and a fourth conduit having a fourth luminal space, wherein a. the vascular channel system and the second vascular channel system are configured to be in fluid communication across the membrane, b. the third conduit has a first end embedded in the biocompatible extracellular matrix of the tissue scaffold and a second end configured to connect to a second fluid supply, c. the fourth conduit has a first end embedded in the biocompatible extracellular matrix of the tissue scaffold and a second end configured to connect to a second fluid outlet, and d. the third luminal space, second vascular channel system, and fourth luminal space are configured to be in fluid communication with each other, the second fluid supply, and the second fluid outlet.

* * * * *